(12) United States Patent
Sato

(10) Patent No.: US 9,974,428 B2
(45) Date of Patent: May 22, 2018

(54) ENDOSCOPE

(71) Applicant: OLYMPUS CORPORATION, Tokyo (JP)

(72) Inventor: Yosuke Sato, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/090,957

(22) Filed: Apr. 5, 2016

(65) Prior Publication Data

US 2016/0213225 A1    Jul. 28, 2016

Related U.S. Application Data

(63) Continuation of application No. PCT/JP2015/063737, filed on May 13, 2015.

(30) Foreign Application Priority Data

May 15, 2014    (JP) .................... 2014-101647

(51) Int. Cl.
*A61B 1/00* (2006.01)
*A61B 1/005* (2006.01)
(Continued)

(52) U.S. Cl.
CPC ............ *A61B 1/0008* (2013.01); *A61B 1/005* (2013.01); *A61B 1/00128* (2013.01);
(Continued)

(58) Field of Classification Search
USPC ......................................... 600/127, 129, 138
See application file for complete search history.

(56) References Cited

U.S. PATENT DOCUMENTS 4,881,810 A * 11/1989 Hasegawa .......... A61B 1/00101
356/241.5
5,193,525 A * 3/1993 Silverstein ......... A61B 1/00096
600/123
(Continued)

FOREIGN PATENT DOCUMENTS

JP    H07-194518 A    8/1995
JP    H07-204157 A    8/1995
(Continued)

OTHER PUBLICATIONS

International Search Report dated Jun. 9, 2015 issued in PCT/JP2015/063737.

*Primary Examiner* — Matthew J Kasztejna
(74) *Attorney, Agent, or Firm* — Scully, Scott, Murphy & Presser, P.C.

(57) ABSTRACT

An endoscope includes: a cylindrical member; a ring member, in which the cylindrical member is fixed; a recess portion provided in an outer circumferential face of the cylindrical member; a first recess wall formed in a direction around an axis in the recess portion; a second recess wall formed along a direction of the axis; a projection portion provided on an inner circumferential face of the ring member, the projection portion being engaged with a recess portion; a first contact portion that comes into contact with the first recess wall in the direction of the axis; and a second contact portion that comes into contact with the second recess wall in the direction around the axis.

12 Claims, 8 Drawing Sheets

(51) Int. Cl.
*A61B 1/018* (2006.01)
*A61B 1/05* (2006.01)
*A61B 1/06* (2006.01)

(52) U.S. Cl.
CPC .............. *A61B 1/018* (2013.01); *A61B 1/051* (2013.01); *A61B 1/0676* (2013.01)

(56) References Cited

U.S. PATENT DOCUMENTS

| | | | | |
|---|---|---|---|---|
| 5,257,617 A * | 11/1993 | Takahashi | .......... | A61B 1/00142 600/123 |
| 5,662,588 A * | 9/1997 | Iida | .................. | A61B 1/00091 600/121 |
| 5,674,181 A * | 10/1997 | Iida | .................... | A61B 1/0008 600/121 |
| 5,725,474 A * | 3/1998 | Yasui | ................ | A61B 1/00091 600/121 |
| 5,725,477 A | 3/1998 | Yasui et al. | | |
| 5,746,695 A * | 5/1998 | Yasui | ................ | A61B 1/00091 600/121 |
| 5,788,628 A * | 8/1998 | Matsuno | .......... | A61B 1/00091 600/121 |
| 5,817,061 A * | 10/1998 | Goodwin | .......... | A61B 17/3417 600/121 |
| 5,846,183 A * | 12/1998 | Chilcoat | ............ | A61B 1/00142 600/112 |
| 5,860,913 A * | 1/1999 | Yamaya | ............. | A61B 1/00091 600/121 |
| 6,004,263 A * | 12/1999 | Nakaichi | ........... | A61B 1/00165 600/120 |
| 6,059,719 A * | 5/2000 | Yamamoto | ......... | A61B 1/00059 600/104 |
| 6,478,731 B2 * | 11/2002 | Speier | ................ | A61B 1/00135 600/121 |
| 6,605,035 B2 * | 8/2003 | Ando | ................... | A61B 1/0008 600/127 |
| 6,921,362 B2 * | 7/2005 | Ouchi | .................... | A61B 1/018 600/121 |
| 7,212,737 B2 * | 5/2007 | Dehmel | ................ | A61B 1/042 348/68 |
| 8,038,604 B2 * | 10/2011 | Hamazaki | ........... | A61B 1/0008 600/107 |
| 8,062,213 B2 * | 11/2011 | Jerjomin | ............ | A61B 1/121 600/127 |
| 9,254,125 B2 * | 2/2016 | Pingleton | ........... | A61B 17/3417 |

FOREIGN PATENT DOCUMENTS

| | | |
|---|---|---|
| JP | 2006-158840 A | 6/2006 |
| JP | 2014-057731 A | 4/2014 |

* cited by examiner

ENDOSCOPE

CROSS REFERENCE TO RELATED APPLICATION

This application is a continuation application of PCT/JP2015/063737 filed on May 13, 2015 and claims benefit of Japanese Application No. 2014-101647 filed in Japan on May 15, 2014, the entire contents of which are incorporated herein by this reference.

BACKGROUND OF THE INVENTION

1. Field of the Invention

The present invention relates to an endoscope in which a structure of a distal end portion of an insertion portion is improved.

2. Description of the Related Art

Insertion apparatuses having an elongated insertion portion which is inserted into a subject are widely used. In some insertion apparatuses, a bending portion is provided on a distal end side of the insertion portion. As an example of the insertion apparatuses, there is an endoscope with which observation and the like can be performed. As shown in FIG. 1, an elongated insertion portion 1 of the endoscope is configured with a distal end portion 2, a bending portion 3, and, for example, a flexible tube portion (not shown) having flexibility arranged from a distal end side in that order and connected to the insertion portion 1.

On a distal end face of the insertion portion 1, an observation window 4 constituting an observation optical system, for example, a pair of illuminating windows 5 constituting an illumination optical system, a distal end opening 6 and the like are provided. Further, some insertion portions are provided with a cleaning nozzle or the like for washing away blood, waste, oil or the like adhering to a surface of the observation window 4 and the like, on the distal end face.

The bending portion 3 is configured having mainly a set of bending pieces, a mesh tube and a bending rubber. The set of bending pieces is configured with a plurality of bending pieces connected so as to bend, for example, in two directions of upward and downward or four directions of upward, downward, right and left.

For example, Japanese Patent Application Laid-Open Publication No. 07-194518 shows an endoscope in which a bending shape of the bending portion is improved so as to facilitate observation and treatment. In the endoscope, a cylindrical body which covers a nozzle, a light guide and an image guide, and a most distal end bending piece are fixed to a rigid distal end component member with fixing screws.

As shown in FIG. 2, an observation optical system hole 8, a treatment instrument insertion hole 9, an illumination optical system hole and an air/water feeding hole which are not shown, and the like are formed in a distal end rigid member 7 constituting the distal end portion 2. An image pickup unit 10 is provided in the observation optical system hole 8.

The image pickup unit 10 is fixed in the observation optical system hole 8, for example, with adhesion; a channel connecting tube 15 is fixed in the treatment instrument insertion hole 9, for example, with adhesion; the light guide is fixed in the illumination optical system hole, for example, with adhesion; and a connecting tube for air/water feeding is fixed in the air/water feeding hole, for example, with adhesion.

The image pickup unit 10 is configured having an objective optical system 13 with a plurality of optical lenses 12 arranged in a lens frame 11, and an image pickup apparatus (not shown) provided with an image pickup device arranged at an image forming position of the objective optical system 13. A proximal end portion of the channel connecting tube 15 projects from a proximal end of the distal end rigid member 7, and a distal end portion of a channel tube 16 is integrally fixed to the proximal end portion. An air feeding tube (not shown) and a water feeding tube (not shown) are integrally fixed to a proximal end portion of the connecting tube for air/water feeding which projects from the proximal end of the distal end rigid member 7.

On an outer circumferential face side of the distal end rigid member 7, a distal end cover 17, a bending rubber 18, and a distal end bending piece 19 are arranged. A flange 7f is provided at a predetermined position of an outer circumference of the distal end rigid member 7. A distal end face of the distal end bending piece 19 is positioned and arranged in contact with a rising surface on a distal end side of the flange 7f. The distal end bending piece 19 is integrally and firmly fixed to the distal end rigid member 7 without backlash by two fixing screws 20 while stress of abutting against the rising surface being generated.

The distal end cover 17 is in a cylindrical shape, and its inner circumferential face is arranged on the outer circumferential face of the distal end rigid member 7. A proximal end face of the distal end cover 17 is arranged at a predetermined position on a more distal end side than the flange 7f. A distal end portion of the bending rubber 18 is arranged on the outer circumferential face of the distal end rigid member 7. A distal end face of the bending rubber 18 is in contact with the proximal end face of the distal end cover 17 arranged on the more distal end side than the flange 7f and integrally and firmly fixed by spool adhesion.

In recent years, high functionality of an endoscope, that is, improvement of observation performance due to increase in the number of pixels, improvement of treatment due to increase in size of a channel tube, addition of a function of cleaning a patient's lesion portion, addition of an enlargement function and the like have been realized. Therefore, in order to expand internal space in the distal end rigid member while realizing a shorter diameter of the insertion portion, the number of screw threads is reduced as far as possible, for example, is set to three, and thickness of a screw head is machined thin to fix a distal end bending piece to the distal end rigid member.

SUMMARY OF THE INVENTION

An endoscope of the present invention includes: a cylindrical member formed in a cylindrical shape extending along a predetermined axis; a ring member in a ring shape, in which the cylindrical member is fixed; a recess portion recessedly provided in an outer circumferential face of the cylindrical member; a first recess wall formed along a direction around the axis of the cylindrical member in the recess portion; a second recess wall formed along a direction of the axis in the recess portion; and a projection portion having an axial-direction contact face that comes into contact with the first recess wall in the direction of the axis and a circumferential-direction contact face that comes into contact with the second recess wall in the direction around the axis, the projection portion inclinedly projecting from an

DETAILED DESCRIPTION OF THE PREFERRED EMBODIMENT

Figure 1:
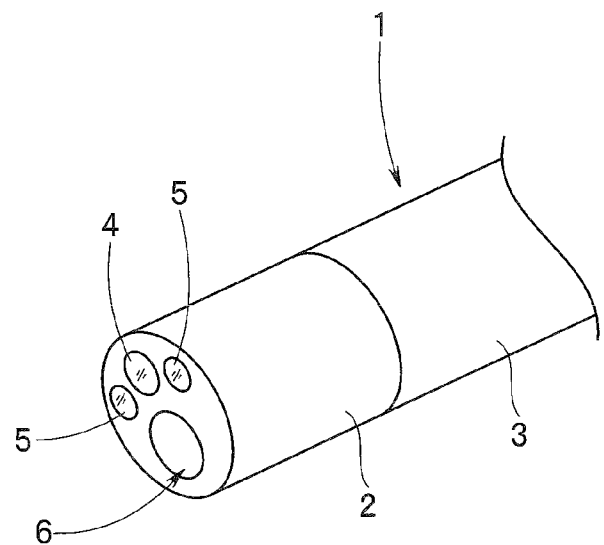
FIG. 1 is a diagram illustrating a distal end portion side of an insertion portion of an endoscope which is an example of an insertion apparatus.
Figure 2:
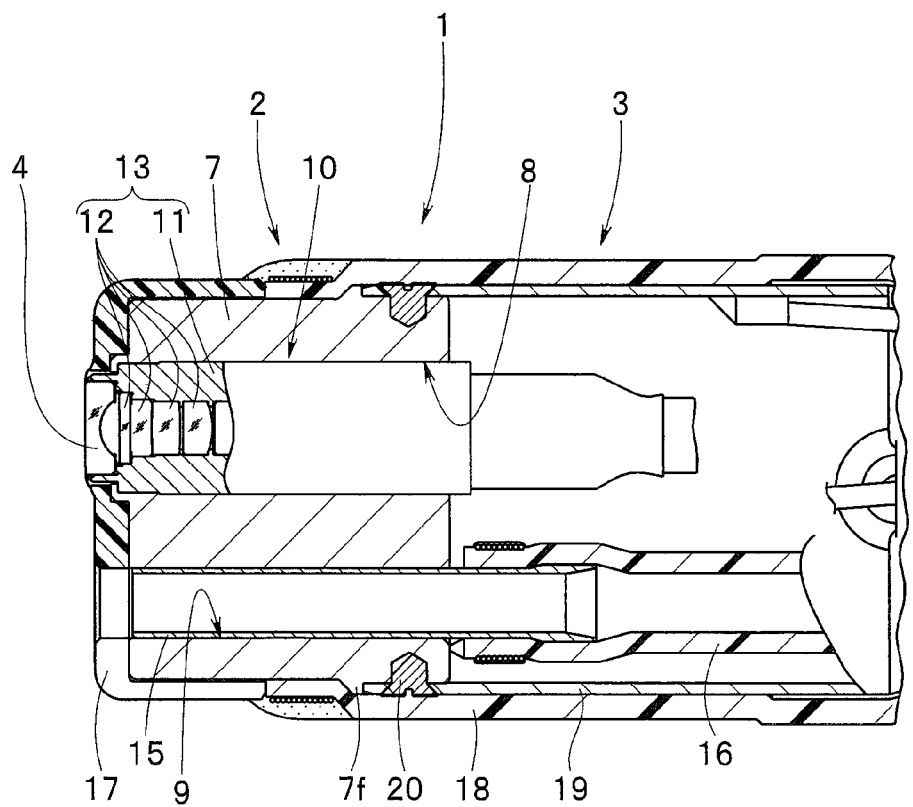
FIG. 2 is a diagram illustrating a configuration of a distal end rigid member having a flange as a positioning portion, and a distal end cover, a bending rubber and a distal end bending piece which are arranged on an outer circumferential face of the distal end rigid member.

An embodiment of the present invention will be described below with reference to drawings.

Note that, in each drawing used in the description below, reduced scale may be different for each component so as to show each component with a size that enables the component to be recognized on the drawing. Further, the present invention is not limited to the number of components, shapes of the components, a ratio among sizes of the components, and relative positional relationships among the respective components shown in the drawings.

Figure 3:
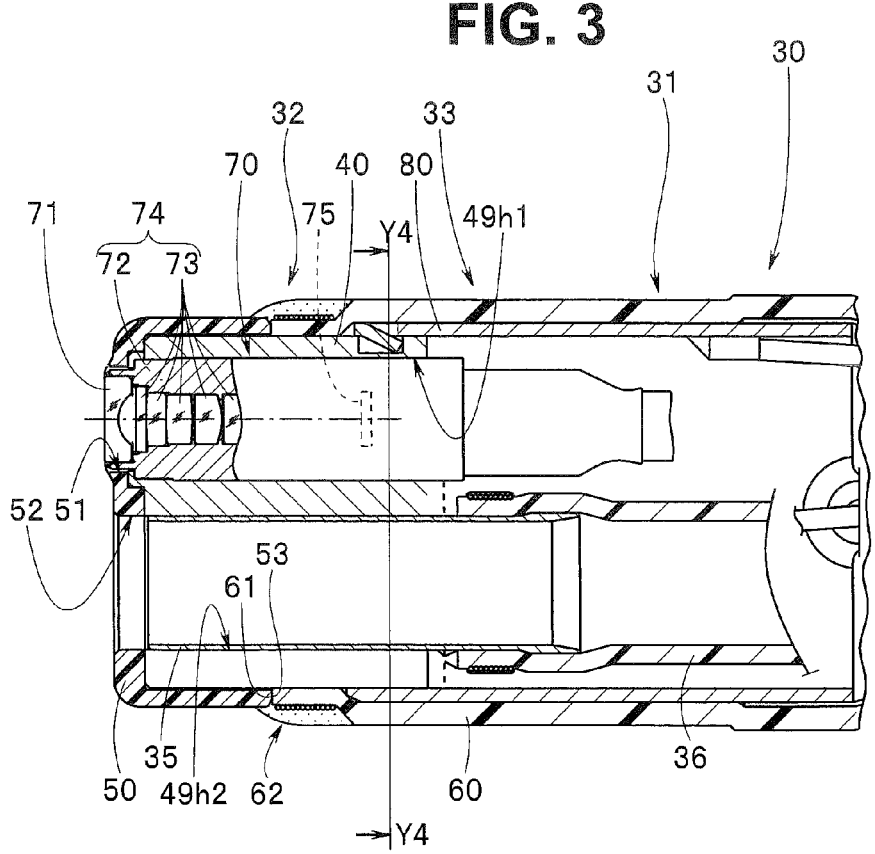
FIG. 3 is a diagram illustrating a distal end rigid member constituting a distal end portion of an insertion portion, and a distal end cover arranged on an outer circumferential face of the distal end rigid member, according to the present invention.
Figure 4:
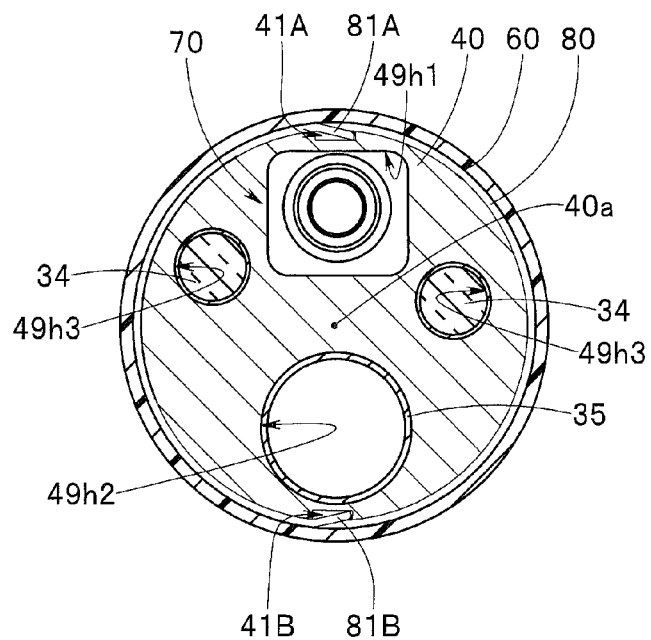
FIG. 4 is a cross-sectional view of a Y4-Y4 line in FIG. 3.

As shown in FIGS. 3 and 4, an insertion portion 31 of an endoscope 30, which is an insertion apparatus of the present invention, is configured having a distal end portion 32, a bending portion 33 and a flexible tube portion not shown from a distal end side in that order. The distal end portion 32 is configured having mainly a distal end rigid member 40, which is a distal end portion body, a distal end cover 50 and a bending rubber 60.

The distal end rigid member 40 is a cylindrical member which is cylindrically formed along a central axis 40a with a metal member, for example, made of stainless steel or the like, and an observation optical system hole 49h1, a treatment instrument insertion hole 49h2, an illumination optical system hole 49h3 and the like are formed in the distal end rigid member 40. A light guide bundle 34 is fixed in the illumination optical system hole 49h3.

A channel connecting tube 35 is fixed in the treatment instrument insertion hole 49h2. An image pickup unit 70 is fixed in the observation optical system hole 49h1.

The image pickup unit 70 is configured having an objective optical system 74 with a plurality of optical lenses 73 arranged in a lens frame 72, and an image pickup apparatus (not shown) provided with an image pickup device 75, such as a CCD and a C-MOS, indicated by a broken line and arranged at an image forming position of the objective optical system 74.

A proximal end portion of the channel connecting tube 35 projects from a proximal end face of the distal end rigid member 40 by a predetermined length. A distal end portion of a channel tube 36 is firmly and integrally fixed to the proximal end portion of the channel connecting tube 35, for example, by spool adhesion.

On an outer circumferential face side of the distal end rigid member 40, the distal end cover 50, a distal end portion of the bending rubber 60 and a distal end part of a distal end bending piece 80 are arranged.

The distal end cover 50 is in a cylindrical shape, and a bottom face of a cylindrical body is arranged on a distal end face of the distal end rigid member 40. Each of an observation hole for observation 51 corresponding to an observation window 71, an illumination hole (not shown) corresponding to an illumination window (not shown), a distal end opening 52 corresponding to the channel connecting tube 35 and the like are formed in the distal end cover 50.

On the other hand, an inner circumferential face of the cylindrical body of the distal end cover 50 is arranged being covered with an outer circumferential face of the distal end rigid member 40. A proximal end face 53 of the distal end cover 50 is arranged at a predetermined position on the outer circumferential face of the distal end rigid member 40.

The distal end bending piece 80 is a piece located at a most distal end of a set of bending pieces configured such that a plurality of bending pieces not shown are rotatably connected so as to bend, for example, in upper, lower, right and left directions. The distal end bending piece 80 is a ring member in a ring shape. The distal end part of the distal end bending piece 80 is arranged being surrounded by a proximal end portion of the distal end rigid member 40. A distal end portion of each of an upward bending wire, a downward bending wire, a left bending wire and a right bending wire which are not shown are fixed at a predetermined position on an inner circumferential face of the distal end bending piece 80.

A configuration of the distal end rigid member 40 and the distal end bending piece 80 will be described with reference to FIGS. 5 to 9.

In the present embodiment, the distal end bending piece 80 and the distal end rigid member 40 have a fixation mechanism of being integrally fixed without use of fastening members such as fixation screws.

Figure 5:
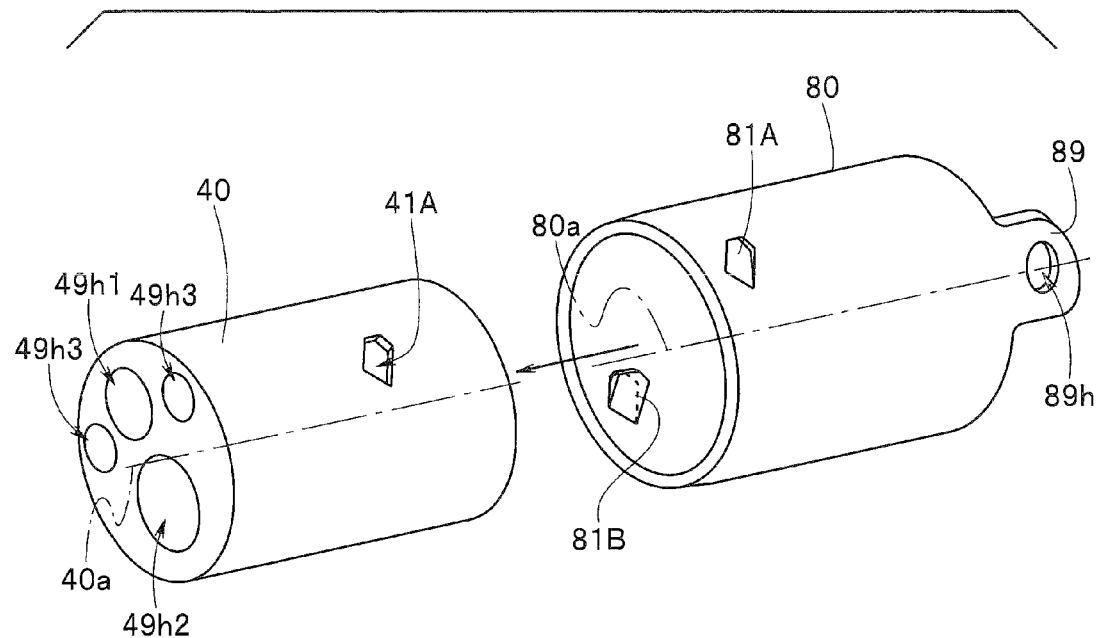
FIG. 5 is a diagram illustrating the distal end rigid member having recess portions and a distal end bending piece having projection portions.

As shown in FIG. 5, a first projection portion 81A and a second projection portion 81B are provided on the distal end bending piece 80 being separated from each other by a predetermine distance relative to a circumferential direction (around the axis). On the other hand, two recess portions 41A and 41B corresponding to the two projection portions 81A and 81B, respectively, are provided on the distal end rigid member 40.

Figure 6:
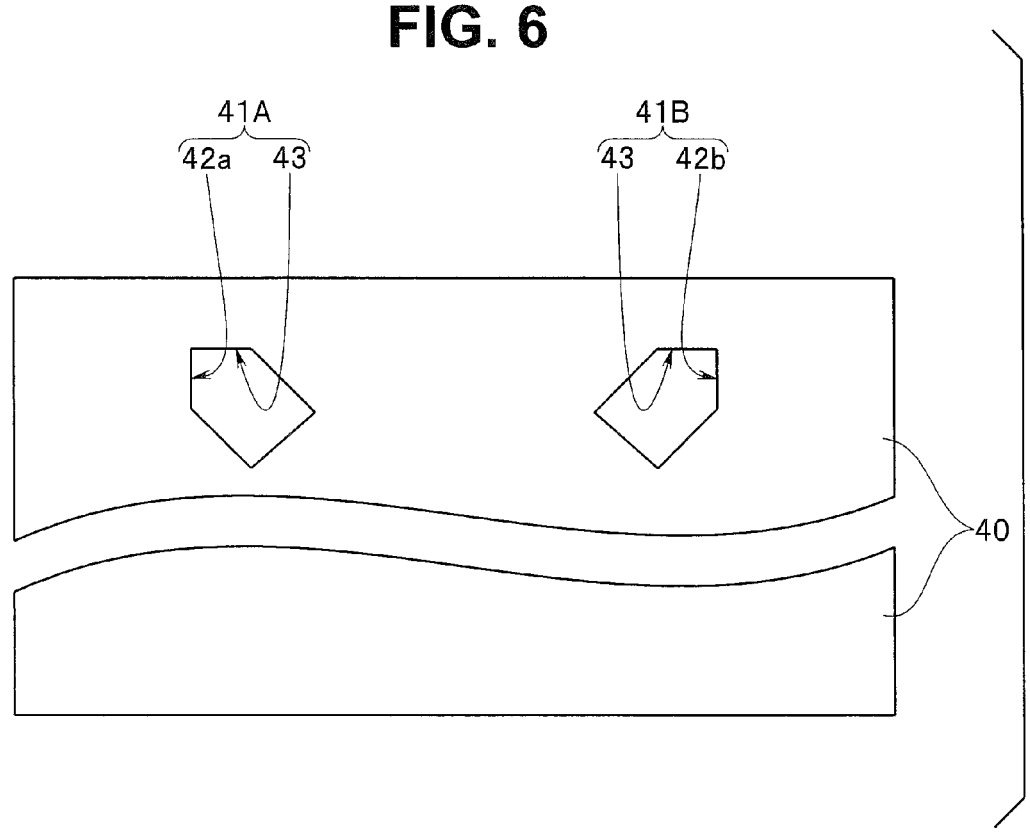
FIG. 6 is a diagram for illustrating positions at which the recess portions are arranged, and is a development diagram of the distal end rigid member.

The recess portions 41A and 41B are hollows as shown in FIGS. 5 and 6. A first circumferential-direction engagement face 42a and an axial-direction engagement face 43 are provided on the first recess portion 41A, and a second circumferential-direction engagement face 42b and an axial-direction engagement face 43 are provided on the second recess portion 41B.

The first circumferential-direction engagement face 42a and the second circumferential-direction engagement face 42b are faces formed by a side vertically toward the central axis 40a (see FIGS. 4 and 5) and a side along the central axis 40a. On the other hand, the axial-direction engagement face 43 is a face formed by a side vertically toward the central axis 40a and a side along a circumferential direction of the distal end rigid member 40.

The first circumferential-direction engagement face 42a and the second circumferential-direction engagement face 42b are formed in a positional relationship of being opposed to each other relative to the circumferential direction.

Note that reference numeral 89 indicates a piece coupling protrusion, and a through hole 89h into which a coupling screw (not shown) is to be inserted is formed in the piece coupling protrusion 89.

Figure 7:
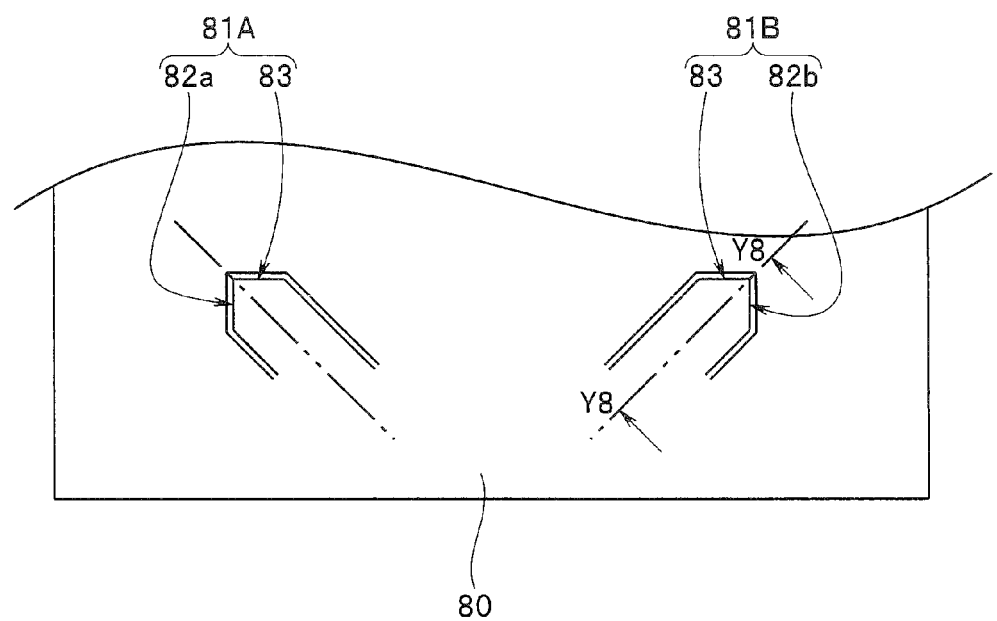
FIG. 7 is a diagram for illustrating positions at which the projection portions are arranged, and is a development diagram of the distal end bending piece.

On the other hand, as shown in FIG. 7, a first circumferential-direction contact face 82a and an axial-direction contact face 83 are provided on a distal end part of the first projection portion 81A, and a second circumferential-direction contact face 82b and an axial-direction contact face 83 are provided on a distal end part of the second projection portion 81B.

Figure 8:
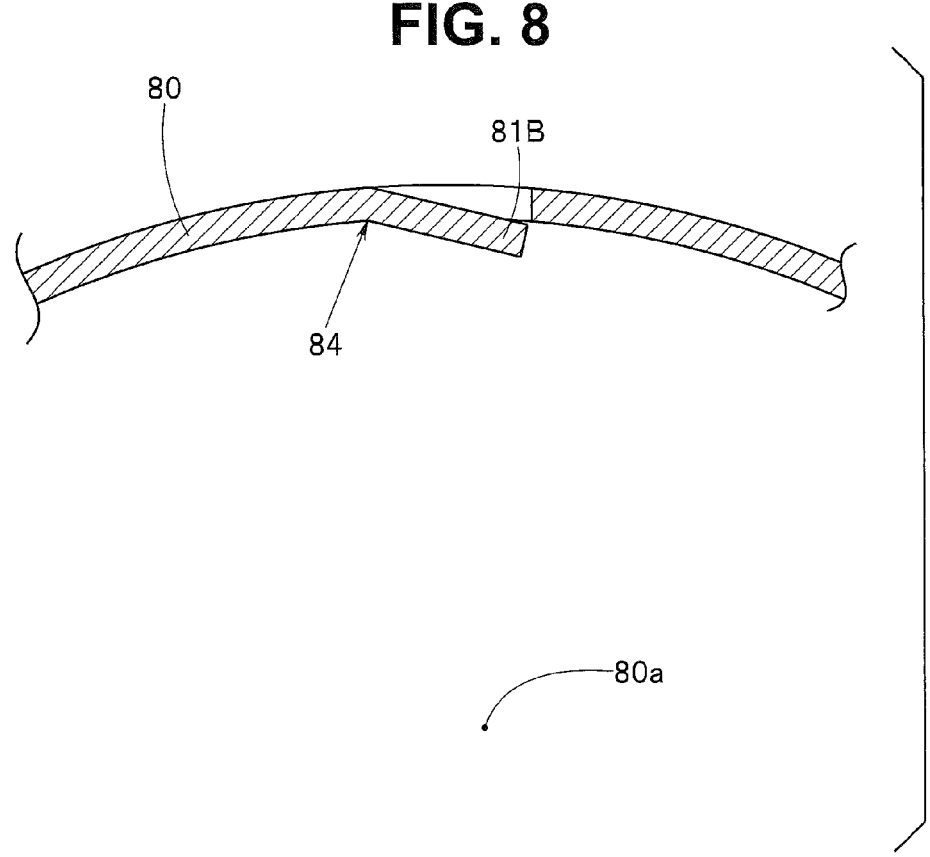
FIG. 8 is a cross-sectional view of a Y8-Y8 line in FIG. 7.

As shown in FIG. 8, the second projection portion 81B is inclinedly cut and raised from a cutting/raising starting point 84 on an inner circumferential face side of the bending piece toward an inner side in a diameter direction, and arranged at a predetermined position on a central axis 80a side of the bending piece 80 shown in FIG. 5, with the distal end part being separated from the inner circumferential face of the distal end bending piece 80 by a predetermined distance.

Note that the projection portion 81A is also inclinedly cut and raised from a cutting/raising starting point not shown toward the inner side in the diameter direction, and arranged at a predetermined position on the central axis 80a side of the bending piece 80, with the distal end part being separated from the inner circumferential face of the distal end bending piece 80 by the predetermined distance.

The projection portions 81A and 81B can be elastically deformed at the cutting/raising starting point 84. The distal end parts of the projection portions 81A and 81B are adapted to be urged by elastic forces of the projection portions 81A and 81B, come into contact with bottom faces of the recess portions 41A and 41B, and be arranged (engaged) in the recess portions 41A and 41B.

Figure 9:
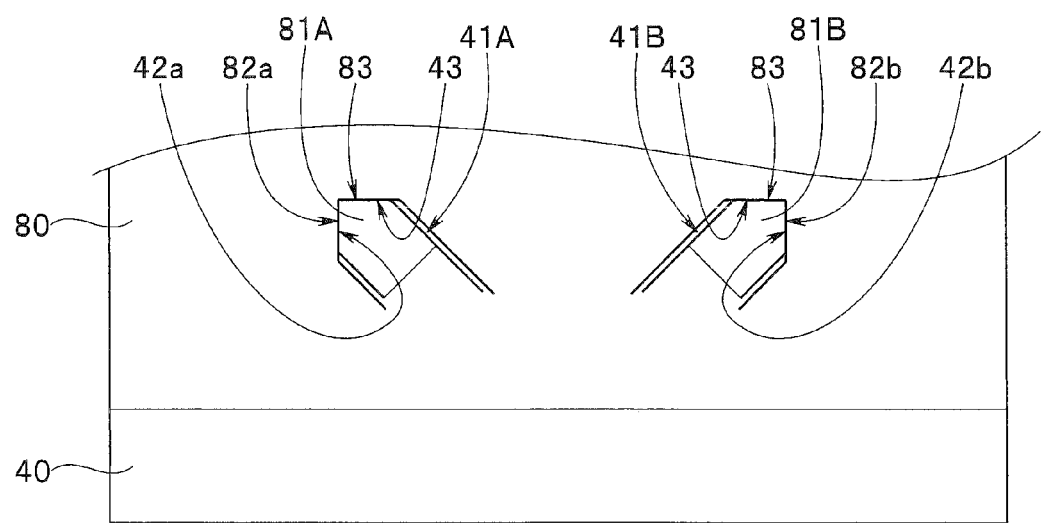
FIG. 9 is a diagram illustrating a state in which second contact portions of the projection portions are arranged in contact with second recess walls of the recess portions, and first contact portions of the projection portions are arranged in contact with first recess walls of the recess portion.

At this time, as shown in FIG. 9, the first circumferential-direction contact face 82a, which is a second contact portion, is urged toward the first circumferential-direction engagement face 42a, which is a second recess wall, in the circumferential direction by the elastic force and arranged in contact with the first circumferential-direction engagement face 42a; the second circumferential-direction contact face 82b, which is the second contact portion, is urged toward the second circumferential-direction engagement face 42b, which is the second recess wall, in the circumferential direction by the elastic force and arranged in contact with the second circumferential-direction engagement face 42b; and the axial-direction contact faces 83, which are first contact portions, are urged toward the axial-direction engagement faces 43, which are first recess walls, in the axial direction by the elastic forces and arranged in contact with the axial-direction engagement faces 43.

Operation of the distal end rigid member 40 having the recess portions 41A and 41B and the distal end bending piece 80 having the projection portions 81A and 81B which are configured as described above will be described.

Figure 10A:
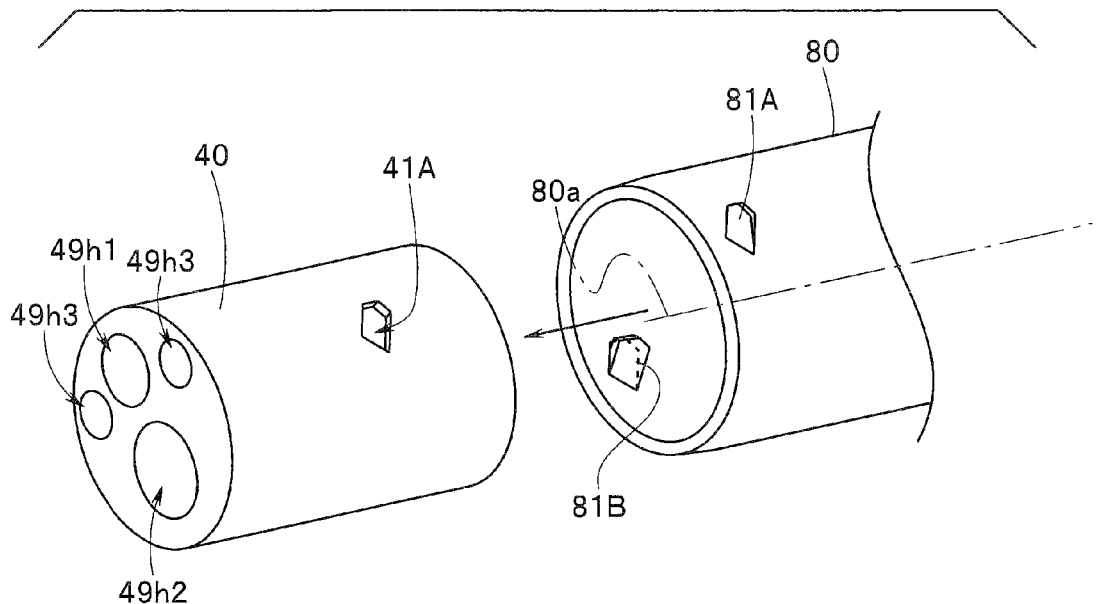
FIG. 10A is a diagram illustrating a procedure for fixing the distal end bending piece to the distal end rigid member.

At time of fixing the distal end bending piece 80 of the set of bending portions to the distal end rigid member 40 into which various components included in the endoscope are extended, a worker causes a distal end face of the distal end bending piece 80 and a proximal end of the distal end rigid member 40 to face each other as shown in FIG. 10A. At this time, the worker aligns a position of the first recess portion 41A with a position of the first projection portion 81A in advance.

Figure 10B:
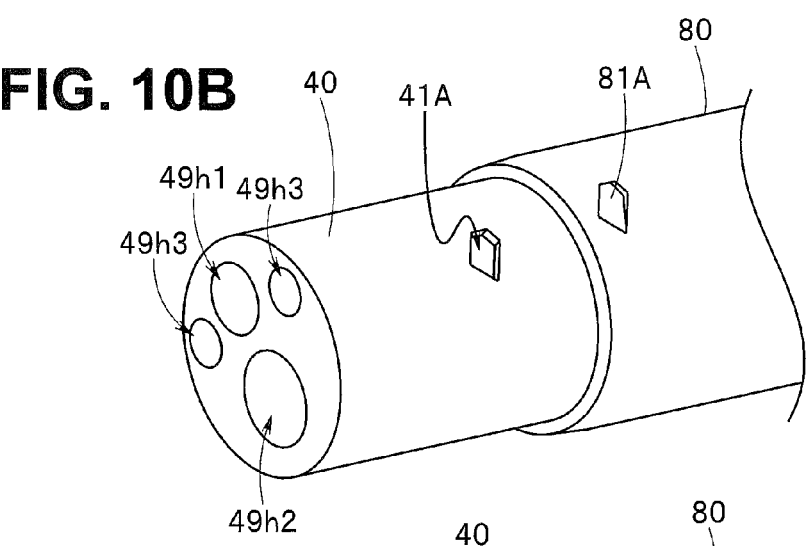
FIG. 10B is a diagram illustrating the procedure for fixing the distal end bending piece to the distal end rigid member.

Next, while keeping the state of alignment between the first recess portion 41A and the first projection portion 81A, the worker covers the distal end face of the distal end bending piece 80 over a proximal-end-side outer circumferential face of the distal end rigid member 40 as shown in FIG. 10B. Then, the worker moves the distal end face of the distal end bending piece 80 to a distal end side of the distal end rigid member 40.

Then, the projection portions 81A and 81B inclinedly projecting from the inner circumferential face of the distal end bending piece 80 toward the central axis 80a side are arranged on the proximal-end-side outer circumferential face of the distal end rigid member 40. After that, the worker moves the distal end bending piece 80 to the distal end side of the distal end rigid member 40. Then, accompanying the movement of the distal end bending piece 80 to the distal end side of the distal end rigid member 40, the projection portions 81A and 81B are elastically deformed. Therefore, the worker further moves the distal end bending piece 80 to the distal end side of the distal end rigid member 40 against the elastic forces of the projection portions 81A and 81B.

Figure 10C:
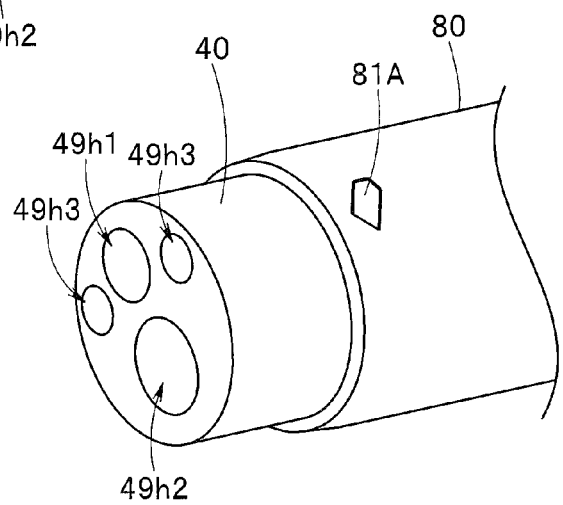
FIG. 10C is a diagram illustrating the procedure for fixing the distal end bending piece to the distal end rigid member.

As a result, distance between the projection portions 81A and 81B, and the recess portions 41A and 41B of the distal end rigid member 40 is gradually shortened; and, at the same time the projection portions 81A and 81B reach the recess portions 41A and 41B, the elastically deformed first projection portion 81A and second projection portion 81B are dropped and arranged into the first recess portion 41A and the second recess portion 41B, respectively, by the elastic forces as shown in FIG. 10C.

At this time, the first circumferential-direction contact face 82a and the second circumferential-direction contact face 82b come into contact with the first circumferential-direction engagement face 42a and the second circumferential-direction engagement face 42b, respectively, as shown in FIG. 9, and come into a state of being pressed. Further, the axial-direction contact faces 83 come into contact with the axial-direction engagement faces 43 and come into a state of being pressed.

Therefore, the distal end bending piece 80 is arranged on the outer circumferential face of the distal end rigid member 40 in a state of being prevented from rotating in clockwise and counterclockwise directions around the central axis 40a of the distal end rigid member 40 and in a state of being prevented from moving along the central axis 40a of the distal end rigid member 40.

After that, the worker covers the bending rubber 60 over the entire length of the flexible tube, the set of bending pieces and the like. At this time, a distal end face 61 of the bending rubber 60 is arranged on the outer circumferential face of the distal end rigid member 40, in contact with the proximal end face 53 of the distal end cover 50 arranged on a more distal end side than the distal end face of the distal end bending piece 80. The distal end portion of the bending rubber 60 firmly and integrally fixed to the distal end rigid member 40 by spool adhesion 62.

As a result, it is possible to integrally fix the distal end bending piece 80 and the distal end rigid member 40 together with a pair of projection portions 81 and a pair of recess portions 41 without use of fastening members such as fixation screws.

Therefore, it is possible to realize reduction in the number of parts. Further, since a distal end bending piece can be provided on a distal end rigid member by dropping and arranging projection portions into recess portions by elastic forces, it is possible to reduce a diameter of an insertion portion or to expand internal space of the distal end rigid member. Further, it is possible to eliminate necessity of work of causing the distal end rigid member, into which components included in the endoscope are extended, to rotate and improve fixation workability.

Note that shapes of the projection portion and the recess portion corresponding to the projection portion are not limited to the shapes shown in FIGS. 5, 9 and the like. For example, the distal end bending piece 80 may be provided with an L-shaped projection portion 81C having a stepped circumferential-direction contact face 84a and an axial-direction contact face 83a as shown in FIG. 11A, a projection portion 81D having a circumferential-direction projection-shaped contact face 85a and a stepped axial-direction contact face 83b as shown in FIG. 11B, a projection portion 81E having a circumferential-direction contact face 86a and a stepped axial-direction contact face 83b as shown in FIG. 11C, a projection portion 81F having a stepped circumferential-direction contact face 87a and an axial-direction projection-shaped contact face 83c as shown in FIG. 11D, an L-shaped projection portion 81G having a circumferential-direction contact face 86a and an axial-direction recess-shaped contact face 83d as shown in FIG. 11E, or the like.

The distal end rigid member 40 is provided with recess portions corresponding to the respective projection portions 81C, 81D, 81E, 81F and 81G though they are not shown.

Further, in the embodiment described above, it is assumed that the first projection portion 81A and the second projection portion 81B are separated from each other by a predetermined distance. However, as shown in FIG. 12A, one projection portion 81AB having the first circumferential-direction contact face 82a, the second circumferential-direction contact face 82b and the axial-direction contact face 83 may be provided as indicated by solid lines, instead of providing the first projection portion 81A and the second projection portion 81B being separated from each other as indicated by broken lines.

Figure 11A:
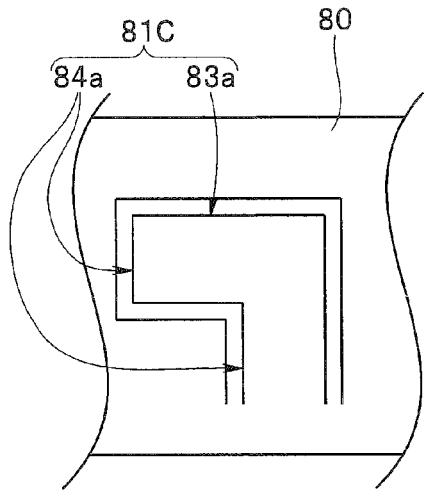
FIG. 11A is a diagram illustrating another configuration example of the projection portion.
Figure 11B:
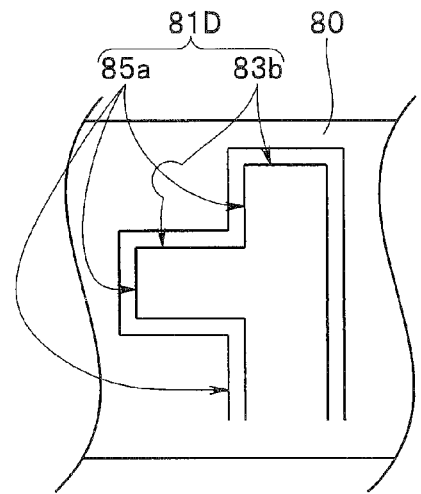
FIG. 11B is a diagram illustrating another configuration example of the projection portion.
Figure 11C:
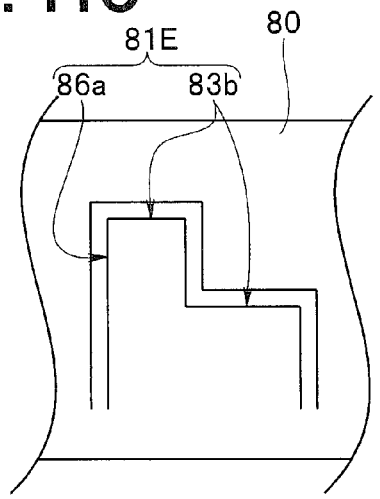
FIG. 11C is a diagram illustrating another configuration example of the projection portion.
Figure 11D:
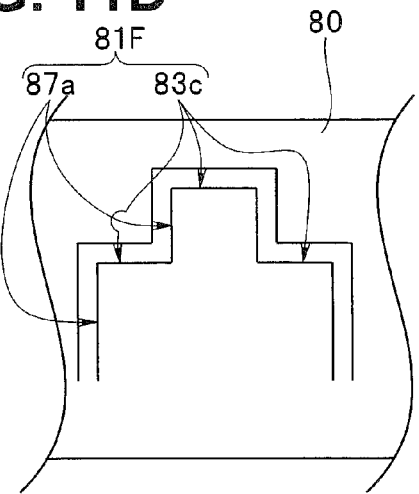
FIG. 11D is a diagram illustrating another configuration example of the projection portion.
Figure 11E:
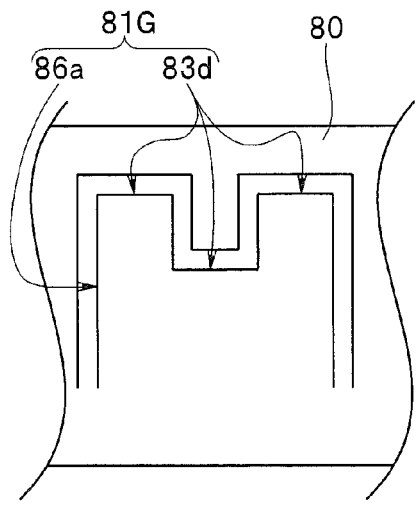
FIG. 11E is a diagram illustrating another configuration example of the projection portion.
Figure 12A:
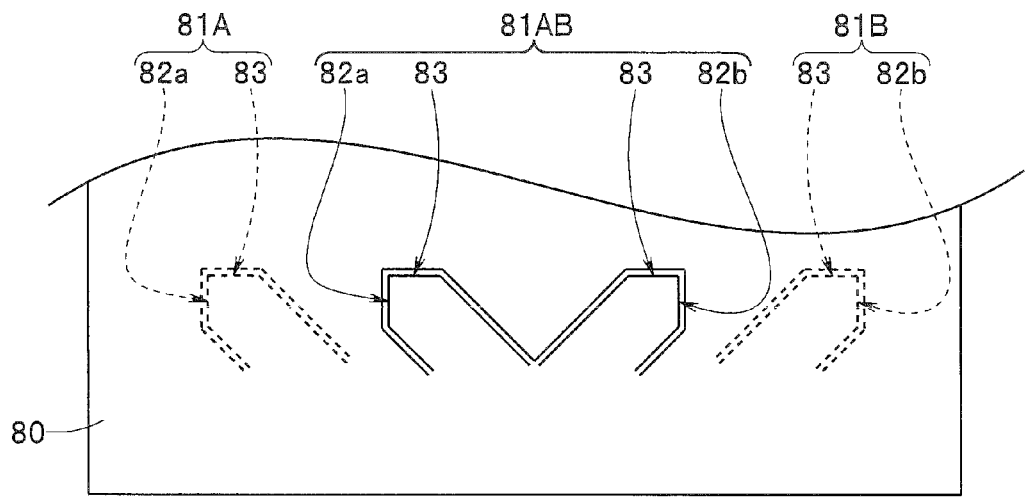
FIG. 12A is a diagram illustrating a configuration example of the projection portion having a first circumferential-direction contact face, a second circumferential-direction contact face and an axial-direction contact face.
Figure 12B:
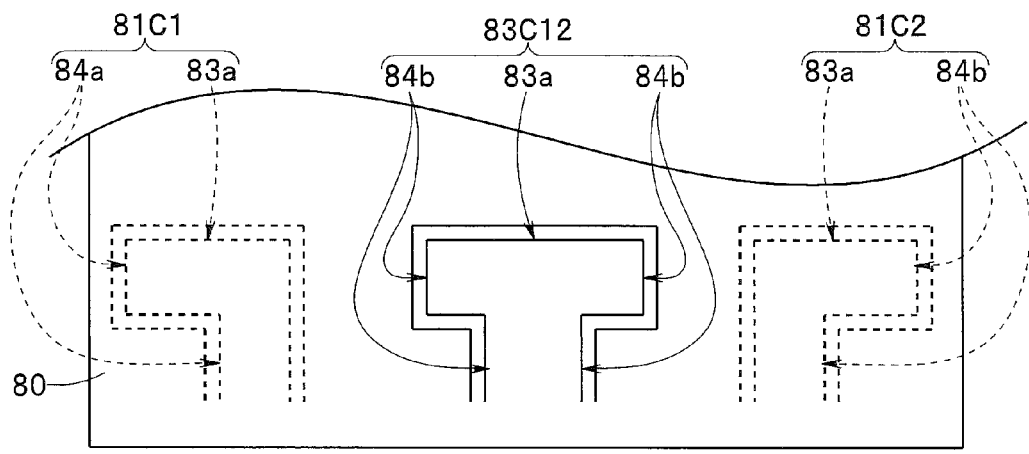
FIG. 12B is a diagram illustrating another configuration example of the projection portion having the first circumferential-direction contact face, the second circumferential-direction contact face and the axial-direction contact face.
Figure 12C:
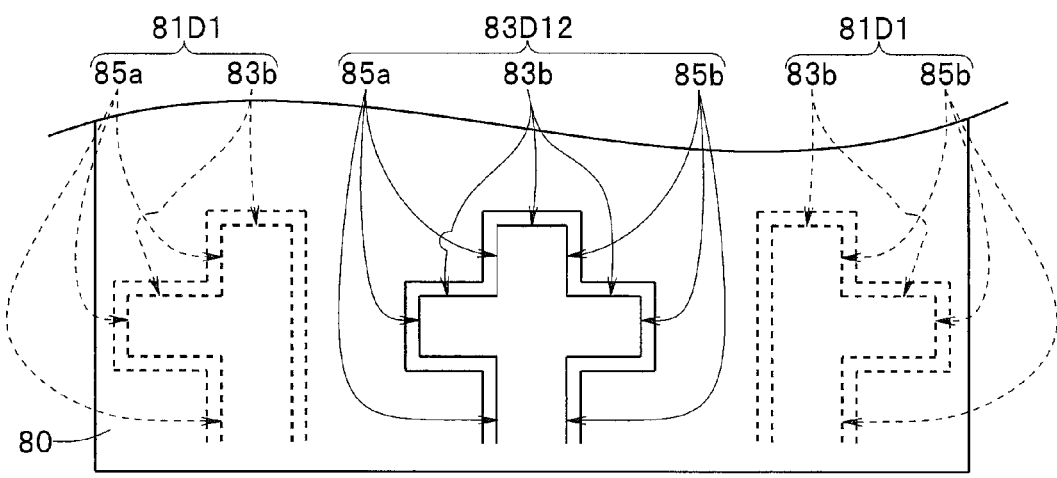
FIG. 12C is a diagram illustrating another configuration example of the projection portion having the first circumferential-direction contact face, the second circumferential-direction contact face and the axial-direction contact face.

Note that a configuration of one projection portion is not limited to FIG. 12A, but it is also possible to configure a first projection portion 81C1 and a second projection portion 81C2 in FIG. 11A described above as one projection portion 83C12 as shown in FIG. 12B or configure a first projection portion 81D1 and a second projection portion 81D2 in FIG. 11B as one projection portion 83D12 or the like as shown in FIG. 12C.

The distal end rigid member 40 is provided with recess portions corresponding to the respective projection portions 81AB, 83C12 and 83D12, though they are not shown.

Further, in a case of providing a plurality of projection portions, for example, two or more projection portions, it is also possible to cause one projection portion to also play a role of a notification portion for notifying, for example, the upward direction of the distal end bending piece 80. In this case, it is not necessary to provide the projection portion to be the notification portion with the face formed by the side vertical to and toward the central axis 40a and the side along the circumferential direction of the distal end rigid member 40, and the projection portion to be the notification portion may be in a D shape, a U shape, a polygon shape such as a triangular shape, a shape obtained by combining the shapes, or the like.

Note that, in the embodiment described above, it is assumed that the insertion apparatus is an endoscope. However, the insertion apparatus is not limited to an endoscope but may be a treatment instrument.

Note that the present invention is not limited to the embodiment described above but may be variously modified and practiced within a range not departing from the spirit of the invention.

According to the present invention, it is possible to realize an endoscope in which the diameter of an insertion portion and the like is reduced, internal space is expanded, and fixation workability is improved.

What is claimed is:

1. An endoscope comprising: a cylindrical member formed in a cylindrical shape extending along a predetermined, central axis, the cylindrical member configured as a distal end rigid member at a distal end of the insertion portion; a ring member in a ring shape, in which the cylindrical member is fixed, the ring member configured as a distal end bending piece of a plurality of bending pieces constituting a bending portion near the distal end of the insertion portion; first and second recessed portions recessedly provided in an outer circumferential face of the cylindrical member; first and second engagement faces, which are each a first recessed wall and formed to extend along a circumferential direction around the central axis of the cylindrical member in the first and the second recessed portions, respectively; third and fourth engagement faces, which are each a second recessed wall and formed to extend along a direction parallel to the central axis in the first and the second recessed portions, respectively; first and second projection portions inclinedly projecting from an inner circumferential face of the ring member toward the central axis side of the ring member; first and second contact faces formed along a circumferential direction of the ring member, configured to come into contact with the first and the second engagement faces in the first and the second recessed portions, respectively; and third and fourth contact faces formed along an axial direction of the ring member, configured to come into contact with the third and the fourth engagement faces in the first and the second recessed portions, respectively, wherein the third and the fourth engagement faces are formed in a positional relationship of being opposed to each other in a circumferential direction, each of the first and the second projection portions is formed by a cut at a part of the ring member, and formed on an incline in a direction toward the central axis from a cutting/raising starting point, and wherein the ring member is in a fixed position with respect to the cylindrical member in a configuration of the first and second projection portions being arranged into the first and the second recessed portions, respectively.

2. The endoscope according to claim 1, wherein the first and the second contact faces are urged toward the first recessed wall.

3. The endoscope according to claim 1, wherein the third and the fourth contact faces are urged toward the second recessed wall.

4. The endoscope according to claim 1, wherein the first and the second projection portions are elastically deformable in the direction of the central axis of and in the direction around the central axis of the ring member.

5. The endoscope according to claim 1, wherein the first and the second projection portions are also used as a fixation indicating portion showing a direction of fixation relative to the cylindrical member.

6. The endoscope according to claim 1, wherein each of the first and the second recessed portions is oriented at an angle offset from perpendicular to the central axis.

7. The endoscope according to claim 1, wherein each of the first and the second projection portions is oriented at an angle offset from perpendicular to the central axis.

8. The endoscope according to claim 1, wherein the first and the second engagement faces and the third and the fourth engagement faces intersect one another.

9. The endoscope according to claim 1, wherein the first and the second contact faces and the third and the fourth contact faces intersect one another.

10. An endoscope comprising an insertion portion, the endoscope comprising:
a cylindrical member formed in a cylindrical shape extending along a predetermined, central axis, the cylindrical member configured as a distal end rigid member at a distal end of the insertion portion;
a ring member in a ring shape, in which the cylindrical member is fixed, the ring member configured as a distal end bending piece of a plurality of bending pieces constituting a bending portion near the distal end of the insertion portion;
first and second recessed portions recessedly provided in an outer circumferential face of the cylindrical member;
first and second engagement faces, which are each a first recessed wall and formed to extend along a circumferential direction around the central axis of the cylindrical member in the first and the second recessed portions, respectively;
third and fourth engagement faces, which are each a second recessed wall and formed to extend along a direction parallel to the central axis in the first and the second recessed portions, respectively;
first and second projection portions inclinedly projecting from an inner circumferential face of the ring member toward the central axis side of the ring member;
first and second contact faces formed on the first and the second projection portions, configured to contact the first and the second engagement faces, respectively; and
third and fourth contact faces formed on the first and the second projection portions, configured to contact the third and the fourth engagement faces, respectively, wherein
the first and the second engagement faces oppose a distal end side of the insertion portion,
the third and the fourth engagement faces are positioned to oppose each other in a circumferential direction,
each of the first and the second projection portions is formed by cutting a part of the ring member into a substantially U-shape with a free end directed toward a proximal end side of the insertion portion, and bending the free end of the ring member toward the central axis from a proximal end of the cut,
the first and the second contact faces and the third and the fourth contact faces of the first and the second projection portions are arranged at the free end of the U-shape, and
the ring member is in a fixed position with respect to the cylindrical member when the first and the second projection portions are arranged in the first and the second recessed portions, respectively.

11. An endoscope comprising:
a cylindrical member formed in a cylindrical shape extending along a predetermined, central axis;
a ring member in a ring shape, in which the cylindrical member is fixed;
two recessed portions recessedly provided in an outer circumferential face of the cylindrical member;
two axial-direction engagement faces, each of which is a first recessed wall formed along a direction parallel to the central axis of the cylindrical member in each of the two recessed portions;
two circumferential-direction engagement faces, each of which is a second recessed wall formed along a circumferential direction around the central axis in each of the two recessed portions; and
two projection portions, each of which has an axial-direction contact face that comes into contact with one of the axial-direction engagement faces in the direction of the central axis and a circumferential-direction contact face that comes into contact with one of the circumferential-direction engagement faces in the direction around the central axis respectively, each of the projection portions inclinedly projecting from an inner circumferential face of the ring member toward the central axis side of the ring member, wherein
the circumferential-direction engagement faces are formed in a positional relationship of being opposed to each other in a circumferential direction,
each of the projection portions formed by a cut at a part of the ring member, and formed on an incline in a direction toward the central axis from a cutting/raising starting point,
wherein the axial-direction contact face and the circumferential-direction contact face are formed on a first end part of each of the projection portions, the first end opposite a second end, the second end attached to the ring member, wherein the ring member is in a fixed position with respect to the cylindrical member when the two projection portions are arranged into the two recessed portions, and wherein each of the recess portions is oriented at an angle offset from perpendicular to the central axis.

12. The endoscope according to claim 11, wherein each of the projection portions is oriented at an angle offset from perpendicular to the central axis.

* * * * *